United States Patent [19]

Martel et al.

[11] 4,307,251

[45] Dec. 22, 1981

[54] PREPARATION OF OPTICALLY ACTIVE ALLETHROLONE

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 155,754

[22] Filed: Jun. 2, 1980

[30] Foreign Application Priority Data

Jun. 12, 1979 [FR] France ............................ 79 14978

[51] Int. Cl.³ ............................................. C07C 45/65
[52] U.S. Cl. ................................................... 568/346
[58] Field of Search ................ 568/341, 346, 838, 913

[56] References Cited

U.S. PATENT DOCUMENTS

| | | | |
|---|---|---|---|
| 3,931,291 | 1/1976 | Horiuchi | 568/346 |
| 3,947,591 | 3/1976 | Matsui et al. | 568/346 |
| 3,981,919 | 9/1976 | Umemura et al. | 568/341 |
| 4,001,334 | 1/1977 | Umemura | 568/341 |
| 4,111,993 | 9/1978 | Pavon et al. | 568/341 |
| 4,128,584 | 12/1978 | Martel et al. | 568/341 |

OTHER PUBLICATIONS

La Forge et al., J.A.C.S., vol. 74, pp. 5392–5394 (1952).

Primary Examiner—Natalie Trousof
Assistant Examiner—James H. Reamer
Attorney, Agent, or Firm—Hammond & Littell, Weissenberger and Muserlian

[57] ABSTRACT

A novel process for the preparation of (R) or (S) 2-allyl-3-methyl-4-hydroxy-2-cyclopentene-1-one comprising reacting a boron halide with an ester of a chiral carboxylic acid of the formula

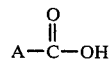

where A is organic group of a chiral carboxylic acid and (R) or (S) 2-allyl-3-methyl-4-hydroxy-2-cyclopentene-1-one and treating the reaction mixture with water to obtain allethrolone with the same configuration of the starting ester in high yields without undesired by-products produced in known methods.

12 Claims, No Drawings

PREPARATION OF OPTICALLY ACTIVE ALLETHROLONE

STATE OF THE ART

The classical methods of obtaining optically active alcohols generally consist in the final step of an acidic or basic hydrolysis to obtain the optically active alcohol. LaForge [J.A.C.S., Vol. 74 (1952), p. 5392] would lead one skilled in the art to expect basic hydrolysis to result with allethrolone to undergo undesired side reactions such as the formation of dimers of allethrolone of the formula

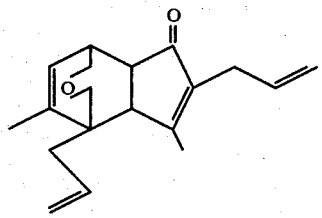

and

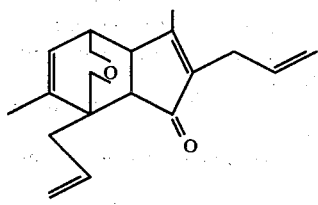

In an acid medium, one skilled in the art would expect the existence of undesired side reactions due to easy protonation of the allylic alcoholic oxygen atom of allethrolone which is particularly reactive leading to the following type of reactions.

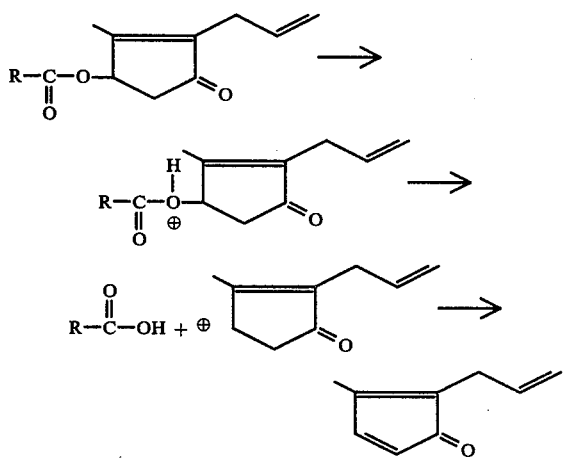

The latter dienic compound is very reactive. Other pertinent art are French Pat. No. 2,223,347 and U.S. Pat. No. 4,111,994.

OBJECTS OF THE INVENTION

It is an object of the invention to provide a novel process for the preparation of pure optically active allethrolone in high yields free of by-products.

This and other objects and advantages of the invention will become obvious from the following detailed description.

THE INVENTION

The novel process for the invention for the preparation of (R) or (S) allethrolone comprises reacting a boron halide with an ester of a chiral carboxylic acid of the formula

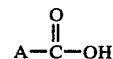

where A is organic group of a chiral carboxylic acid and (R) or (S) 2-allyl-3-methyl-4-hydroxy-2-cyclopentene-1-one and treating the reaction mixture with water to obtain allethrolone with the same configuration of the starting ester.

The chiral carboxylic acid of the formula

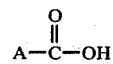

may be an aliphatic carboxylic acid or a carboxylic acid containing one or more rings such as an acid of polycyclanic structure, steroid structure or a cyclopropane carboxylic acid.

Examples of specific chiral carboxylic acids whose esters are useful in the process of the invention are 2,2-dimethyl-3-(2-methyl-1-propenyl)-cyclopropane-1-carboxylic acids, 2,2-dimethyl-3-(2,2-dibromovinyl)-cyclopropane-1-carboxylic acids, 2,2-dimethyl-3-(2,2-dichlorovinyl)-cyclopropane-1-carboxylic acids, 2,2-dimethyl-3-cyclobutylidenemethylcyclopropane-1-carboxylic acids, 2,2-dimethyl-3-cyclopentylidenemethyl-cyclopropane-1-carboxylic acids, 2,2-dimethyl-3-fluorenylidenemethyl)-cyclopropane-1-carboxylic acids, 2,2-dimethyl-3-(2-oxo-3-oxa-cyclopentylidenemethyl-cyclopropane-1-carboxylic acids, 2,2-dimethyl-3-(2,2-difluorovinyl)-cyclopropane-1-carboxylic acids and 2-(3-chlorophenyl)-2-isopropylacetic acids. The preferred acid is 2,2-dimethyl-3R-(2-methyl-1propenyl)-cyclopropane-1R-carboxylic acid.

The boron halide may be especially boron tribromide or boron trichloride. The reaction is preferably effected in an organic solvent such as methylene chloride at temperatures of about −40° C. to 0° C., most preferably about −20° C. Preferably, 2 or more moles of the boron halide per mole of ester are used.

The process of the invention permits the scission of the esters under very mild conditions to obtain pure allethrolone in high yields free of by-products that occur in the classical methods of preparing optically active isomers of allethrolone.

In the following example there are described several preferred embodiments to illustrate the invention. However, it should be understood that the invention is not intended to be limited to the specific embodiments.

EXAMPLE (4S) 2-allyl-3-methyl-4-hydroxy-2-cyclopentene-1-one 1.5 g of (4S) 2-allyl-3-methyl-2-cyclopentene-1-one-4-yl 2,2-dimethyl-3R-(2-methyl-1-propenyl)-cyclopropane-1R-carboxylate was added to 15 ml of methylene chloride and then 7.8 ml of a methylene chloride solution of 1.6 M of boron trichloride was slowly added to the mixture at −20° C. The mixture was stirred at −12° C. for 3 hours and was then poured into an ice-water mixture. The mixture was stirred for 15 hours and the pH was adjusted to 10 by addition of dilute sodium hydroxide. The aqueous phase was saturated with sodium chloride and was then extracted with methylene chloride. The organic phase was dried and evaporated to dryness and the residue was chromatographed over silica gel. Elution with a 7-3 benzene ethyl acetate mixture yielded 530 mg of (4S) 2-allyl-3-methyl-4-hydroxy-2-cyclopentene-1-one with a specific rotation of $[\alpha]_D^{20} = +5°$ (c=1.2% in benzene).

UV Spectrum (ethanol):
 Max. at 230 nm $E_1^1 = 810$
 Max. at 308 nm $E_1^1 = 4$ Circular Dichroism (dioxane):
 $\Delta\epsilon = -18.6$ at 231 nm (max.)
 $\Delta\epsilon = +3.19$ at 322 nm (max.)
 $\Delta\epsilon = +2.93$ at 332 nm (max.)

Various modifications of the process of the invention may be made without departing from the spirit or scope thereof and it should be understood that the invention is intended to be limited only as defined in the appended claims.

We claim:

1. A process for the preparation of (R) or (S) allethrolone comprising reacting at least two moles of a boron halide with one mole of an ester of a chiral carboxylic acid of the formula

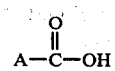

where A is the organic group of a chiral carboxylic acid and (R) or (S) 2-allyl-3-methyl-4-hydroxy-2-cyclopentene-1-one at −40° to 0° C. in an organic solvent and treating the reaction mixture with water to obtain allethrolone with the same configuration of the starting ester.

2. The process of claim 1 wherein the chiral carboxylic acid is an aliphatic carboxylic acid.

3. The process of claim 1 wherein the chiral carboxylic acid contains at least one ring.

4. The process of claim 3 wherein the chiral carboxylic acid has a polycyclanic structure.

5. The process of claim 3 wherein the chiral carboxylic acid has a steroid structure.

6. The process of claim 3 wherein the chiral carboxylic acid has a cyclopropane structure.

7. The process of claim 1 wherein the chiral carboxylic acid is selected from the group consisting of 2,2-dimethyl-3-(2-methyl-1-propenyl)-cyclopropane-1-carboxylic acids, 2,2-dimethyl-3-(2,2-dibromovinyl)-cyclopropane-1-carboxylic acids, 2,2-dimethyl-3-(2,2-dichlorovinyl)-cyclopropane-1-carboxylic acids, 2,2-dimethyl-3-cyclobutylidenemethylcyclopropane-1-carboxylic acids, 2,2-dimethyl-3-cyclopentylidenemethyl-cyclopropane-1-carboxylic acids, 2,2-dimethyl-3-fluorenylidenemethyl-cyclopropane-1-carboxylic acids, 2,2-dimethyl-3-(2-oxo-3-oxa-cyclopentylidenemethyl-cyclopropane-1-carboxylic acids, 2,2-dimethyl-3-(2,2-difluorovinyl)-cyclopropane-1-carboxylic acids and 2-(3-chlorophenyl)-2-isopropylacetic acids.

8. The process of claim 1 wherein the chiral carboxylic acid is 2,2-dimethyl-3R-(2-methyl-1-propenyl)-cyclopropane-1R-carboxylic acid.

9. The process of claim 1 wherein the boron halide is boron tribromide.

10. The process of claim 1 wherein the boron halide is boron trichloride.

11. The process of claim 1 wherein the boron halide reaction is effected at −40° to 0° C. in methylene chloride.

12. The process of claim 11 wherein the temperature is about −20° C.

* * * * *